US012733909B2

(12) United States Patent
Zhou et al.

(10) Patent No.: US 12,733,909 B2
(45) Date of Patent: Sep. 15, 2026

(54) 4D INTRACARDIAC ECHOCARDIOGRAPHY IMAGING SYSTEM, ECHOCARDIOGRAPHY IMAGING METHOD AND ECHOCARDIOGRAPHY IMAGING APPARATUS

(71) Applicant: Shenzhen Cardioacc Ltd, Shenzhen (CN)

(72) Inventors: Xinhuan Zhou, Guangdong (CN); Jun Ma, Guangdong (CN); Jia Mei, Guangdong (CN)

(73) Assignee: Shenzhen Cardioacc Ltd, Guangdong (CN)

(*) Notice: Subject to any disclaimer, the term of this patent is extended or adjusted under 35 U.S.C. 154(b) by 119 days.

(21) Appl. No.: 18/727,564

(22) PCT Filed: Sep. 7, 2023

(86) PCT No.: PCT/CN2023/117407
§ 371 (c)(1),
(2) Date: Jan. 8, 2025

(87) PCT Pub. No.: WO2024/114021
PCT Pub. Date: Jun. 6, 2024

(65) Prior Publication Data

US 2025/0120674 A1 Apr. 17, 2025

(30) Foreign Application Priority Data

Nov. 29, 2022 (CN) ......................... 202211508883.8

(51) Int. Cl.
*A61B 8/00* (2006.01)
*A61B 8/08* (2006.01)
(Continued)

(52) U.S. Cl.
CPC ............ *A61B 8/445* (2013.01); *A61B 8/0883* (2013.01); *A61B 8/12* (2013.01); *A61B 8/4461* (2013.01);
(Continued)

(58) Field of Classification Search
CPC ......... A61B 8/445; A61B 8/0883; A61B 8/12; A61B 8/4461; A61B 8/4488; A61B 8/54;
(Continued)

(56) References Cited

U.S. PATENT DOCUMENTS

2008/0287803 A1* 11/2008 Li .......................... A61B 5/064 382/128
2008/0312536 A1* 12/2008 Dala-Krishna .......... A61B 8/12 600/459

(Continued)

FOREIGN PATENT DOCUMENTS

CN 101779965 A * 7/2010
CN 103393437 A 11/2013

(Continued)

OTHER PUBLICATIONS

International Search Report, China National Intellectual Property Administration, Oct. 30, 2023.

*Primary Examiner* — Kaitlyn E Sebastian
(74) *Attorney, Agent, or Firm* — Bay State IP, LLC

(57) ABSTRACT

Provided by the present disclosure are a 4D (four-dimensional) intracardiac echocardiography (ICE) imaging system, an ultrasonic imaging method and an ultrasonic imaging apparatus. The system at least includes an interventional catheter, an external mechanical driving apparatus, and an ultrasonic host. The interventional catheter includes a miniature ultrasonic probe located at a distal end. The ultrasonic host is connected to the miniature ultrasonic probe, and used to output an acoustic wave driving signal. The miniature
(Continued)

ultrasonic probe is used to emit the acoustic wave driving signal intermittently. The mechanical driving apparatus is used to drive the probe to rotate unidirectionally and uniformly in the interventional catheter when the probe emits the acoustic wave driving signal, thus performing mechanical 4D scanning imaging. The miniature ultrasonic probe is also used to receive an echo signal of the acoustic wave driving signal, and to transmit the echo signal to the ultrasonic host.

7 Claims, 5 Drawing Sheets

(51) Int. Cl.
*A61B 8/12* (2006.01)
*G01S 15/89* (2006.01)

(52) U.S. Cl.
CPC ........ *A61B 8/4488* (2013.01); *G01S 15/8934* (2013.01); *G01S 15/8993* (2013.01)

(58) Field of Classification Search
CPC ....... A61B 8/483; A61B 8/48; G01S 15/8934; G01S 15/8993
See application file for complete search history.

(56) References Cited

U.S. PATENT DOCUMENTS

2014/0180124 A1* 6/2014 Whiseant ............. A61B 8/0883 600/467
2016/0374710 A1* 12/2016 Sinelnikov ......... A61B 17/3207 600/439
2017/0354395 A1* 12/2017 Lupotti ................ A61B 8/4461

FOREIGN PATENT DOCUMENTS

CN 112004496 A 11/2020
CN 112566557 A 3/2021
CN 114748103 A 7/2022

* cited by examiner

4D INTRACARDIAC ECHOCARDIOGRAPHY IMAGING SYSTEM, ECHOCARDIOGRAPHY IMAGING METHOD AND ECHOCARDIOGRAPHY IMAGING APPARATUS

CROSS REFERENCE TO RELATED APPLICATION

This application is for entry into the U.S. National Phase from which priority is claimed under all applicable sections of Title 35 of the United States Code including, but not limited to, Sections 120, 363, and 365(c) to International Application No. PCT/CN2023/117407 filed on Sep. 7, 2023, and which in turn claims priority under 35 USC 119 to Chinese Patent Application No. CN202211508883.8 filed on Nov. 29, 2022, the contents of which are incorporated by reference herein in its entirety as part of the present application.

TECHNICAL FIELD

The present disclosure relates to the technical field of ultrasound imaging, and in particular to a 4D (four-dimensional) intracardiac echocardiography imaging system, an ultrasonic imaging method and an ultrasonic imaging apparatus.

BACKGROUND

Electrophysiological heart disease and structural heart disease are major human health problems. Electrophysiological heart disease is usually arrhythmia caused by irregular current transmission in the heart, while structural heart disease is heart disease caused by cardiac structural abnormalities (e.g., myocardial hypertrophy, atrial septal defect, and left atrial appendage thrombosis). Interventional therapy with minimally invasive catheter is the first-line treatment of electrophysiological heart disease and structural heart disease at present. Interventional catheter (e.g., microwave/radio frequency/pulsed electric field/balloon ablation, artificial valve and occluder) is inserted into the cardiac chamber by peripheral vascular intervention for treatment. As there is no need for thoracotomy, interventional catheter intervention can reduce the surgical risk and postoperative recovery cost. Due to the rapid three-dimensional movement of the heart during the intervention, 4D cardiac imaging (i.e., dynamic 3D (three-dimensional) imaging) is performed during the operation, and relative positions of the interventional catheter and the cardiac chamber can be monitored in real time. Compared with 2D (two-dimensional) imaging, the 4D cardiac imaging is more intuitive and has a dynamic three-dimensional field of vision, can monitor the surgical complications (such as thrombosis and pericardial effusion) in real time, and has important clinical significance.

Intracardiac echocardiography (ICE) is the most advanced cardiac imaging technology in clinic. By inserting a miniature ultrasonic probe into the cardiac chamber through the femoral vein, the heart can be imaged in real time and in high definition. 4D ICE is the technical development direction of the next generation of ICE. At present, 4D ICE used in clinic usually uses a matrix-phase array transducer. The probe includes numerous ultrasonic transducer units arranged in two dimensions, and can be used to scan and image a region of interest by electronically deflecting the ultrasonic beam. Area array probe can achieve real-time and high-depth three-dimensional imaging, but its probe is high in integration and complex in process. On the other hand, the probe contains numerous ultrasonic array elements, and each array element needs a separate lead wire. In order to reduce the number of wire harnesses of the transducer, it is usually necessary to integrate a disposable application-specific integrated chip (ASIC) at the front end of the interventional catheter for imaging signal processing. The ASIC chip is high in development and production cost, and generally has serious heating problem, which limit the acoustic emission power.

Therefore, there are some problems in achieving 4D imaging at present, such as high cost, large device volume, large amount of data processed and high computational complexity. The existing 4D imaging technology still has room for improvement to facilitate rational use of resources.

SUMMARY

A main objective of the present disclosure is to provide a 4D ICE imaging system, an ultrasonic imaging method and an ultrasonic imaging apparatus, which can solve the problem of high cost and large volume in the prior art.

To achieve the objective above, in a first aspect, the present disclosure provides a 4D ICE imaging system. The 4D ICE imaging system at least includes an interventional catheter, an external mechanical driving apparatus, and an ultrasonic host. The interventional catheter includes a cavity located at a distal end, and a miniature ultrasonic probe located in the cavity, and the mechanical driving apparatus is arranged at a proximal end of the interventional catheter. The mechanical driving apparatus and the ultrasonic host are connected to the miniature ultrasonic probe, respectively.

The ultrasonic host is used to output an acoustic wave driving signal.

The miniature ultrasonic probe is used to intermittently emit the acoustic wave driving signal output by the ultrasonic host.

The mechanical driving apparatus is used to drive the miniature ultrasonic probe to rotate unidirectionally and uniformly inside the interventional catheter when the miniature ultrasonic probe emits the acoustic wave driving signal output by the ultrasonic host, thus performing mechanical 4D scanning imaging on different positions of an imaging target.

The miniature ultrasonic probe is also used to receive an echo signal of the acoustic wave driving signal, and to transmit the received echo signal to the ultrasonic host; and the ultrasonic host is also used to perform signal post-processing on the received echo signal to determine 4D ultrasonic imaging of the imaging target.

In a feasible implementation mode, an inner wall of the interventional catheter includes at least four drawing wires with an interval of 90°. The proximal end of the interventional catheter is also provided with a handle, and the handle is used to pull at least one of the drawing wires to adjust tightness of the drawing wire, thus achieving the bending of the miniature ultrasonic probe in four directions.

In a feasible implementation mode, the 4D ICE imaging system further includes a torque coil, and a catheter-side connector. The torque coil is arranged in the cavity of the interventional catheter and fixedly connected to the miniature ultrasonic probe, and the torque coil is fixedly connected to the catheter-side connector. The catheter-side connector rotates to drive the torque coil and the probe to rotate. The miniature ultrasonic probe, the torque coil and the catheter-side connector are all disposable.

In a feasible implementation mode, the mechanical driving apparatus includes a motor, a multichannel slip ring, and a host-side connector. The motor is fixedly connected to a stator of the multichannel slip ring, and the host-side connector is fixedly connected to a rotor of the multichannel slip ring. The host-side connector is connected to the catheter-side connector, the motor drives the rotor of the multichannel slip ring to rotate through mechanical transmission, and the motor, the multichannel slip ring and the host-side connector are all reusable.

In a feasible implementation mode, the miniature ultrasonic probe is a two-dimensional imaging phased array probe, or multiple two-dimensional imaging phased array probes combined at a preset spatial angle.

In a feasible implementation mode, the miniature ultrasonic probe includes a transducer, and an acoustic lens. The acoustic lens is used to focus an ultrasonic wave emitted by the transducer to enhance a signal-to-noise ratio of the ultrasonic wave at a focusing position.

In a feasible implementation mode, the cavity of the interventional catheter is filled with normal saline in a manner of filling the normal saline into the cavity at the distal end of the interventional catheter through a syringe at the proximal end of the interventional catheter, thus achieving acoustic coupling between the transducer and an outer sheath of the interventional catheter.

To achieve the objective above, in a second aspect, an ultrasonic imaging method is provided, which is applied to the 4D ICE imaging system in the first aspect or any feasible implementation mode. The ultrasonic imaging method includes the following steps:

- acquiring an echo signal, where the echo signal is that, when a mechanical driving apparatus drives a miniature ultrasonic probe to rotate uniformly and unidirectionally, the miniature ultrasonic probe emits an acoustic wave driving signal intermittently and receives an echo signal;
- performing signal post-processing which includes filtering and beamforming on the echo signal to obtain a beamformed image;
- acquiring spherical coordinates of each voxel point of the beamformed image according to a rotation speed of the mechanical driving apparatus and time of receiving the echo signal; and
- interpolating the voxel points expressed in the spherical coordinates by a preset interpolation algorithm, and transforming the spherical coordinates of the voxel points in a spherical coordinate system into image pixels in Cartesian coordinate system to obtain a 4D ultrasonic image of an imaging target composed of the image pixels.

In a feasible implementation mode, the interpolation algorithm further includes the following mathematical expression:

$$
\begin{aligned}
C = &\\
& V(\rho_i, \theta_j, \varphi_k)(1-\rho_d)(1-\theta_d)(1-\varphi_d) + V(\rho_{i+1}, \theta_j, \varphi_k)\rho_d(1-\theta_d)(1-\varphi_d) + \\
& V(\rho_i, \theta_j, \varphi_{k+1})(1-\rho_d)(1-\theta_d)\varphi_d + V(\rho_{i+1}, \theta_j, \varphi_{k+1})\rho_d(1-\theta_d)\varphi_d + \\
& V(\rho_i, \theta_{j+1}, \varphi_k)(1-\rho_d)\theta_d(1-\varphi_d) + V(\rho_{i+1}, \theta_j+1, \varphi_k)\rho_d\theta_d(1-\varphi_d) + \\
& V(\rho_i, \theta_{j+1}, \varphi_{k+1})(1-\rho_d)\theta_d\varphi_d + V(\rho_{i+1}, \theta_j+1, \varphi_k)\rho_d\theta_d\varphi_d;
\end{aligned}
$$

where $\rho_d=(\rho-\rho_i)/(\rho_{i+1}-\rho_i)$, $\theta_d=(\theta-\theta_j)/(\theta_{j+1}-\theta_j)$, $\varphi_d=(\varphi-\varphi_k)/(\varphi_{k+1}-\varphi_k)$, $(\rho_i, \theta_j, \varphi_k)$ is the spherical coordinates, C are image pixels on the Cartesian coordinate system (x, y, z).

In order to achieve the objective above, in a third aspect, an ultrasonic imaging apparatus is provided, which includes:

- a signal acquisition signal, used to acquire an echo signal, where the echo signal is that, when a mechanical driving apparatus drives a miniature ultrasonic probe to rotate uniformly and unidirectionally, the miniature ultrasonic probe emits an acoustic wave driving signal intermittently and receives an echo signal;
- a beamforming module, used to perform signal post-processing which includes filtering and beamforming on the echo signal to obtain a beamformed image;
- a coordinate calculation module, used to acquire spherical coordinates of each voxel point of the beamformed image according to a rotation speed of the mechanical driving apparatus and time of receiving the echo signal; and
- a coordinate transformation module, used to interpolate the voxel points represented in the spherical coordinates by a preset interpolation algorithm, and transform the spherical coordinates of the voxel points in a spherical coordinate system into image pixels in Cartesian coordinate system to obtain a 4D ultrasonic image of an imaging target composed of image pixels.

In order to achieve the objective above, in a fourth aspect, a computer readable storage medium is further disclosed. A computer program is stored in the computer readable storage medium. The computer program, when executed by a processor, enables the processor to execute the steps of the ultrasonic imaging method above.

The implementation of the embodiment of the present disclosure will have the following beneficial effects:

A 4D ICE imaging system is provided, at least including an interventional catheter, an external mechanical driving apparatus, and an ultrasonic host. The interventional catheter includes a cavity located at a distal end, a miniature ultrasonic probe located in the cavity, and the mechanical driving apparatus is arranged at a proximal end of the interventional catheter. The mechanical driving apparatus and the ultrasonic host are connected to the miniature ultrasonic probe, respectively. The ultrasonic host is used to output an acoustic wave driving signal. The miniature ultrasonic probe is used to emit the acoustic wave driving signal output by the ultrasonic host intermittently. The mechanical driving apparatus is used to drive the miniature ultrasonic probe to rotate unidirectionally and uniformly inside the interventional catheter when the miniature ultrasonic probe emits the acoustic wave driving signal output by the ultrasonic host, thus performing mechanical 4D scanning imaging on different positions of an imaging target. The miniature ultrasonic probe is also used to receive an echo signal of the acoustic wave driving signal, and to transmit the received echo signal to the ultrasonic host. The ultrasonic host is also used to perform signal post-processing on the received echo signal to determine 4D ultrasonic imaging of the imaging target. The above imaging system can achieve the 4D ultrasonic imaging of the imaging target. As the miniature ultrasonic probe and the mechanical driving apparatus are arranged at the proximal end of the interventional catheter, an outer diameter of the interventional catheter is effectively reduced, and thus during the intervention therapy, the complexity of the probe and the system and the cost of the surgical instrument can be reduced while ensuring the 4D ultrasonic imaging of the imaging target.

BRIEF DESCRIPTION OF THE DRAWINGS

To describe the technical solutions of the present disclosure or in the prior art more clearly, the following briefly introduces the accompanying drawings required for describing the embodiments or the prior art. Apparently, the accompanying drawings in the following description show merely some embodiments of the present disclosure, and those of ordinary skill in the art may still derive other drawings from these accompanying drawings without creative efforts.

In the drawings:

FIG. 2(*b*) is a structural schematic diagram of an ultrasonic probe according to an embodiment of the present disclosure;

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the scope of protection of the present disclosure.

Figure 1:
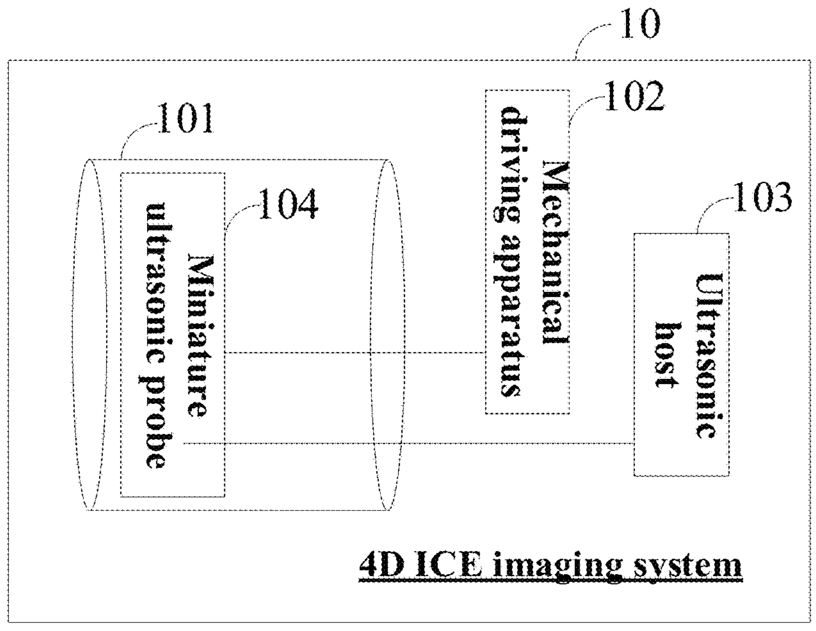
FIG. 1 is a structural schematic diagram of a 4D ICE imaging system according to an embodiment of the present disclosure.

Please referring to FIG. 1, FIG. 1 is a structural schematic diagram of a 4D ICE imaging system according to an embodiment of the present disclosure. The 4D ICE imaging system 10 shown in FIG. 1 at least includes an interventional catheter 101, an external mechanical driving apparatus 102, and an ultrasonic host 103. The interventional catheter 101 includes a cavity located at a distal end, and a miniature ultrasonic probe 104 located in the cavity. The mechanical driving apparatus 102 is arranged at a proximal end of the interventional catheter 101. The mechanical driving apparatus 102 and the ultrasonic host 103 are connected to the miniature ultrasonic probe 104, respectively.

It should be noted that the interventional catheter 101 is inserted into the body by an interventional method, such that the miniature ultrasonic probe 104 at the distal end of the interventional catheter 101 can enter the body together for in vivo 4D ultrasonic imaging of an imaging target, such as a cardiovascular interventional catheter. The interventional catheter 101 is inserted into a cardiac chamber by peripheral vascular intervention for 4D ultrasonic imaging. The imaging target includes, but is not limited to, the cardiac chamber, and the types of interventional catheters also include, but are not limited to, cardiovascular interventional catheter. The interventional catheter 101 usually has two ends, one end is used to intervene in the body, the other end is left outside the body. The end that intervenes in the body is called the distal end, and the end that stays outside the body is called the proximal end, i.e., the distal end and the proximal end of the interventional catheter 101 in this embodiment, which are referred to relative to a user operating the interventional catheter, such as a doctor or an experimenter.

Further, the ultrasonic host 103 is used to output an acoustic wave driving signal, and to transmit the acoustic wave driving signal to the miniature ultrasonic probe 104. The acoustic wave driving signal is emitted out by the miniature ultrasonic probe 104. Exemplary, the ultrasonic host 103 may be an electronic device capable of emitting ultrasonic waves.

The miniature ultrasonic probe 104 is used to emit the acoustic wave driving signal output by the ultrasonic host 103 intermittently for two-dimensional imaging. The so-called emission means that the acoustic wave driving signal is converted into acoustic energy to be emitted. Meanwhile, the mechanical driving apparatus 102 is used to drive the miniature ultrasonic probe 104 to rotate unidirectionally and uniformly inside the interventional catheter 101 when the miniature ultrasonic probe 104 emits the acoustic wave driving signal output by the ultrasonic host 103, thus performing mechanical 4D scanning imaging on different positions of an imaging target. Further, the miniature ultrasonic probe 104 is also used to receive an echo signal of the acoustic wave driving signal output by the ultrasonic host 103, and to transmit the received echo signal to the ultrasonic host 103. The ultrasonic host 103 is also used to perform signal post-processing on the received echo signal to determine 4D ultrasonic imaging, rendering and dynamic display of the imaging target.

It may be understood that the rotation of the mechanical driving apparatus 102 can change an emitting direction of the acoustic wave signal. If the mechanical driving apparatus 102 rotates, 4D ultrasonic imaging can be achieved, and if the mechanical driving apparatus 102 does not rotate, 2D ultrasonic imaging can be achieved.

A 4D ICE imaging system is provided, at least including an interventional catheter, an external mechanical driving apparatus, and an ultrasonic host. The interventional catheter includes a cavity located at a distal end, a miniature ultrasonic probe located in the cavity, and the mechanical driving apparatus is arranged at a proximal end of the interventional catheter. The mechanical driving apparatus and the ultrasonic host are connected to the miniature ultrasonic probe, respectively. The ultrasonic host is used to output an acoustic wave driving signal. The miniature ultrasonic probe is used to emit the acoustic wave driving signal output by the ultrasonic host intermittently. The mechanical driving apparatus is used to drive the miniature ultrasonic probe to rotate unidirectionally and uniformly inside the interventional catheter when the miniature ultrasonic probe emits the acoustic wave driving signal output by the ultrasonic host, thus performing mechanical 4D scanning imaging on different positions of an imaging target. The miniature ultrasonic probe is also used to receive an echo signal of the acoustic wave driving signal, and to transmit the received echo signal to the ultrasonic host. The ultrasonic host is also used to perform signal post-processing on the received echo signal to determine 4D ultrasonic imaging of the imaging target. The above imaging system can achieve the 4D ultrasonic imaging of the imaging target. As the miniature ultrasonic probe and the mechanical driving apparatus are arranged at the proximal end of the interventional catheter, an outer diameter of the interventional catheter is effectively reduced, and thus during the intervention therapy, the complexity of the probe and the system and the cost of the surgical instrument can be reduced while ensuring the 4D ultrasonic imaging of the imaging target.

Figure 2:
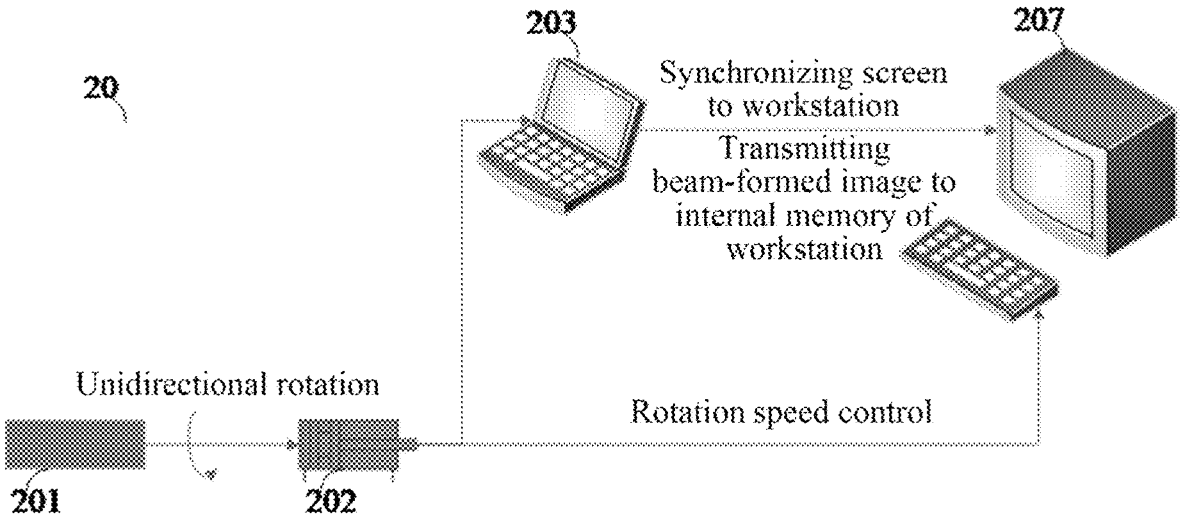
FIG. 2(*a*) is another structural schematic diagram of a 4D ICE imaging system according to an embodiment of the present disclosure.
Figure 2B:
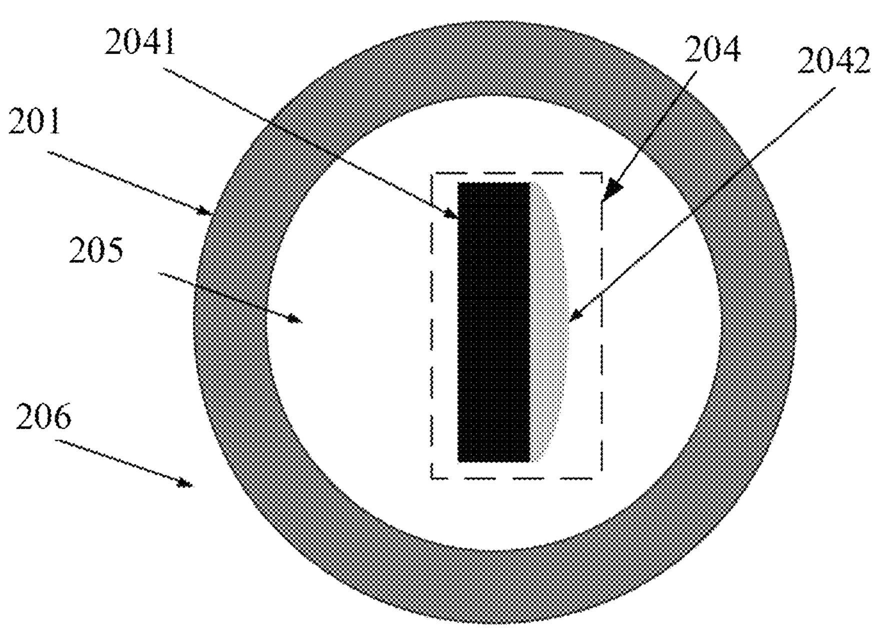

Please referring to FIG. 2 (*a*) and FIG. 2 (*b*), FIG. 2 (*a*) is another structural schematic diagram of a 4D ICE imaging system according to an embodiment of the present disclosure, and FIG. 2 (*b*) is a structural schematic diagram of an ultrasonic probe according to an embodiment of the present disclosure. FIG. 2 (*b*) may also be a sectional diagram of the interventional catheter. Further, the 4D ICE imaging system 20 shown in FIG. 2 (*a*) and FIG. 2 (B) at least includes an interventional catheter 201, an external mechanical driving apparatus 202, and an ultrasonic host 203. The interventional catheter 201 includes a cavity located at a distal end, and a miniature ultrasonic probe 204 located in the cavity; and the mechanical driving apparatus 202 is arranged at a proximal end of the interventional catheter 201. The mechanical driving apparatus 203 and the ultrasonic host 203 are connected to the miniature ultrasonic probe 204, respectively.

The ultrasonic host 203 is used to output an acoustic wave driving signal, and the miniature ultrasonic probe 104 is used to emit the acoustic wave driving signal output by the ultrasonic host 103 intermittently. The mechanical driving apparatus 202 is used to drive the miniature ultrasonic probe 204 to rotate unidirectionally and uniformly inside the interventional catheter 201 when the miniature ultrasonic probe 204 emits the acoustic wave driving signal output by the ultrasonic host 203, thus performing mechanical 4D scanning imaging on different positions of an imaging target. The miniature ultrasonic probe 204 is also used to receive an echo signal of the acoustic wave driving signal, and to transmit the received echo signal to the ultrasonic host 203. The ultrasonic host 203 is also used to perform signal and image post-processing on the received echo signal to determine 4D ultrasonic imaging of the imaging target. For example, a 4D image is obtained through the echo signal, and the obtained image is displayed on a display screen through rendering and other image processing means.

It should be noted that the interventional catheter 201, the mechanical driving apparatus 202, the ultrasonic host 203 and the miniature ultrasonic probe 204 are similar in content to the interventional catheter 101, the mechanical driving apparatus 102, the ultrasonic host 103 and the miniature ultrasonic probe 104 shown in FIG. 1, which will not be described in detail here for avoiding repetition, and can specifically refer to the content of the interventional catheter 101, the mechanical driving apparatus 102, the ultrasonic host 103 and the miniature ultrasonic probe 104 shown in FIG. 1.

Figure 3:
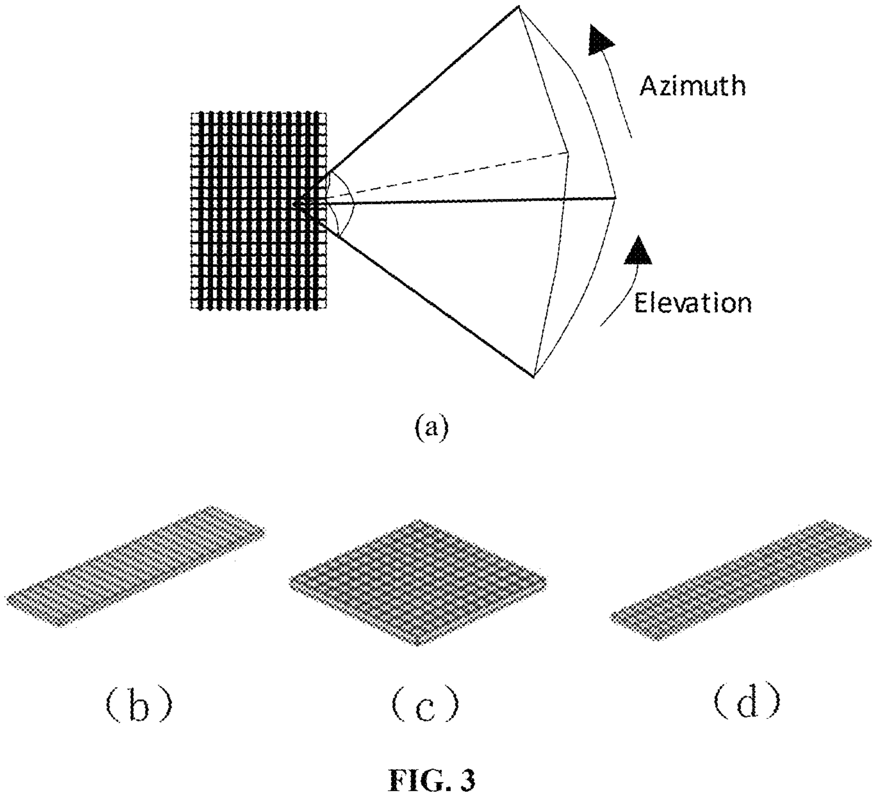
FIG. 3 is a structural schematic diagram of imaging of an area array probe according to an embodiment of the present disclosure.

Further, the miniature ultrasonic probe 204 includes a transducer 2041, and an acoustic lens 2042. The acoustic lens 2042 covers on the transducer 2041, and is used to focus ultrasonic waves emitted by the transducer 2041, thus enhancing the signal-to-noise ratio of the ultrasonic waves at a certain deep focusing position. The acoustic focusing in a direction perpendicular to an imaging plane is adjusted through the acoustic lens 2042 on the probe, an imaging window with the maximum rotation direction of 360° can be achieved by adjusting the imaging window in a rotation direction by software. The miniature ultrasonic probe 204 is a two-dimensional imaging phased array probe, or multiple two-dimensional imaging phased array probes combined at a preset spatial angle, where the arrangement mode may be back-to-back arrangement. Exemplary, referring to FIG. 3, FIG. 3 is a schematic diagram of imaging of an area array probe according to an embodiment of the present disclosure. FIG. 3 (*a*) shows volumetric Imaging of a matrix ultrasonic probe. FIG. 3 (*b*) is a linear phased array probe, FIG. 3 (*c*) is a two-dimensional area array, and FIG. 3 (*d*) is a 1.5D area array.

It should be noted that the commonly used 4D ICE probe generally uses the area array ultrasonic probes such as the two-dimensional area array and 1.5D probe in FIG. 3 (*c*) and FIG. 3 (*d*), respectively. Theses probes are arranged into two dimensions, and can perform dynamic three-dimensional volumetric Imaging.

Moreover, the above area array probe has numerous elements, usually 1024 array elements or 840 array elements. The smaller the ICE probe, the less the puncture injury to the patient during the surgery, about 1000 array elements are integrated on the probe with a width of only about 3 mm, and the integration degree and technology of the probe are complicated and the cost is high. On the other hand, each array element requires a separate lead wire to achieve separate excitation and signal reception, and about 1000 lead wires cannot be led out of a catheter of about 3 mm. In order to reduce the number of the lead wires, an ASIC chip needs to be added on the probe for signal preprocessing, thus outputting a preprocessed signal from the catheter with less lead wires. These processes lead to the difficulty and high cost of array 4D ICE. Meanwhile, as the problems of large amount of data of the probe, complex post-processing, the heating of application specific integrated circuit (ASIC) are difficult to solve, and the host cost is high.

In order to reduce the cost of the area array 4D ICE, a technology to achieve cardiac 4D imaging by mechanical rotation is provided by the present disclosure. The used ultrasonic probe is a two-dimensional imaging probe (linear-phase array transducer) in FIG. 3 (*b*). The probe includes a small number of transducer units arranged linearly, and deflection, scanning and imaging in the direction perpendicular to the imaging plane are realized by mechanical rotation, thus greatly reducing the integration difficulty and the number of probes. On the other hand, due to the large amount of data and high computation complexity, an image three-dimensional reconstruction algorithm based on high-performance parallel computing provided by the present disclosure can greatly improve the post-processing speed of the mechanical 4D ICE. It may be understood that the ultrasonic probe in this embodiment may be a two-dimensional imaging probe, a two-dimensional area array ultrasonic transducer, or other transducers such as ultrasonic linear arrays, circular arrays, convex arrays and 1.5D. The transducer material is PZT (porous lead zirconate titanate) ceramic, or a composite material, PMUT (piezoelectric micromachined ultrasonic transducer), CMUT (Capacitive micromachined ultrasonic transducer), or other novel probe materials.

Further, the cavity of the interventional catheter 201 is filled with normal saline 205 in a manner of filling the normal saline into the cavity at the distal end of the interventional catheter through a syringe at the proximal end of the interventional catheter, thus achieving acoustic coupling between the transducer and an outer sheath of the interventional catheter. Exemplary, the interventional catheter 201 may be Pebax catheter. After the interventional catheter is inserted into the body, an outer wall of the catheter is generally in contact with body fluid 206, where the body fluid 206 may be blood. The transducer and the acoustic lens rotate unidirectionally in the Pebax catheter, and the catheter keeps stationary.

Exemplary, the rotation mode may be unidirectional rotation, or bidirectional reciprocating rotation.

In a feasible implementation mode, an inner wall of the interventional catheter 201 includes at least four drawing wires with an interval of 90° (not shown in the figure), and a handle (not shown in the figure) is also provided at the proximal end of the interventional catheter. The handle is used for pulling at least one drawing wire to adjust the tightness of the drawing wire to achieve angle deflection, i.e., bending in four directions, of the miniature ultrasonic probe, thus imaging different positions of an imaging target. The imaging target includes, but is not limited to, heart, cardiac chamber, and the like. The handle may be provided with a rotary knob, and the tightness of the drawing wire is adjusted by adjusting the rotary knob. A front end of the catheter is made of a flexible material, a rear end of the catheter is made of a relatively hard material, and the drawing wire is embedded in the catheter. When the drawing wire is pulled, the deflection can be achieved as the flexible material at the front end can be bent, and the relatively hard material at the rear end does not bend. Exemplary, the bendable handle may be a four-way bendable handle, or a two-way bendable handle.

In a feasible implementation mode, the mechanical driving apparatus 202 includes a motor, a multichannel slip ring, and a host-side connector. The motor is fixedly connected to a stator of the multichannel slip ring, the host-side connector is fixedly connected to a rotor of the multichannel slip ring, and the host-side connector is connected to the catheter-side connector. The motor drives the rotor of the multichannel slip ring to rotate through mechanical transmission, and the motor, the multichannel slip ring and the host-side connector are all reusable.

It should be noted that the as the motor and multichannel slip ring of the mechanical driving apparatus cannot enter the body, the mechanical driving apparatus can be used repeatedly for many times, and does not need to be replaced every time after the catheter is inserted into the body. Moreover, as the motor and multichannel slip ring are expensive devices, the repeated use can also save cost and achieve rational resource utilization.

Further, the motor in this scheme is deployed at an ultrasonic host side for repeated use, and the linear-phase array ultrasonic probe located at a tip end of the catheter is driven to rotate by the torque coil located in the catheter, thus achieving low-cost 4D imaging. In order to reduce the performance requirement and host cost of the ultrasonic host and improve the post-processing speed of mechanical 4D imaging, a three-dimensional reconstruction algorithm based on high-performance parallel computing is provided, the three-dimensional reconstruction, rendering and other algorithms requiring high computing power are completed on a back-end parallel computing workstation (e.g., CPU (central processing unit) workstation or GPU (graphic processing unit)), such that the portable ultrasonic host with low cost can be used and the device cost of the hospital can be reduced, which will be discussed later.

In a feasible implementation mode, the 4D ICE imaging system further includes a torque coil, and a catheter-side connector. The torque coil is arranged in the cavity of the interventional catheter and fixedly connected to the miniature ultrasonic probe, and the torque coil is fixedly connected to the catheter-side connector. The catheter-side connector rotates to drive the torque coil and the probe to rotate. The miniature ultrasonic probe, the torque coil and the catheter-side connector are all disposable.

It should be noted that the miniature ultrasonic probe, the torque coil and the catheter-side connector intervening into the human body can be replaced. For example, the miniature ultrasonic probe, the torque spring and the catheter-side connector will be replaced for different interveners, which are disposable. The uniform and unidirectional rotation of the probe in the catheter can be achieved through the slip ring and the torque coil, and the rotating motor is placed outside the proximal catheter and reused to prevent the lead wire of the probe in unidirectional rotation from twisting. On the one hand, the cost of consumables and the size of the catheter can be reduced. On the other hand, a larger closed-loop control motor can be used to improve the accuracy of rotational imaging.

The fixed connection includes, but is not limited to, welding. As the torque coil and the transducer cannot move relative to each other, the torque coil and the transducer can be welded generally. The connector includes a consumable-side connector and a host-side connector. In general, the spring and the consumable-side connector are welded.

Further, in order to improve the imaging efficiency, the 4D ICE imaging system may also include a workstation 207 for 4D ultrasonic imaging. Therefore, the ultrasonic host can synchronize the screen to the work station, and thus the beamformed image can be transmitted to an internal memory of the workstation for subsequent ultrasonic imaging method, thus obtaining the 4D ultrasonic imaging of the imaging target. The ultrasonic imaging method will be described later. The rotation speed of the motor can be controlled by the workstation, which is not limited thereto.

A 4D ICE imaging system is provided, at least including an interventional catheter, an external mechanical driving apparatus, and an ultrasonic host. The interventional catheter includes a miniature ultrasonic probe at a distal end, and the mechanical driving apparatus includes a motor and a multichannel slip ring. The mechanical driving apparatus is arranged at a proximal end of the interventional catheter. The mechanical driving apparatus and the ultrasonic host are connected to the miniature ultrasonic probe, respectively. The ultrasonic host is used to output an acoustic wave signal. The miniature ultrasonic probe is used to emit the acoustic wave signal output by the ultrasonic host. The mechanical driving apparatus is used to drive the miniature ultrasonic probe to rotate unidirectionally and uniformly inside the interventional catheter when the miniature ultrasonic probe emits the acoustic wave signal output by the ultrasonic host, thus performing mechanical 4D scanning imaging on an imaging target. The miniature ultrasonic probe is also used to receive an echo signal of the acoustic wave signal, and to transmit the received echo signal to the ultrasonic host. The ultrasonic host is also used to determine 4D ultrasonic imaging of the imaging target. The motor in closed-loop control is located at the proximal end of the catheter, with adjustable rotation speed. The unidirectional rotation of the motor drives a rotor portion of the slip ring to rotate, and drives the torque coil and the probe to rotate unidirectionally and uniformly through the connector. The handle is used to regulate an angle of an imaging window of the probe through the drawing wire. The ultrasonic probe can rapidly rotate unidirectionally and uniformly during rapid imaging, the collected signal is transmitted to a portable ultrasonic host for beamforming through a lead wire, and the data after beamforming is transmitted to the workstation for interpolation three-dimensional reconstruction and rendering and display based on high-performance parallel computing.

Figure 4:
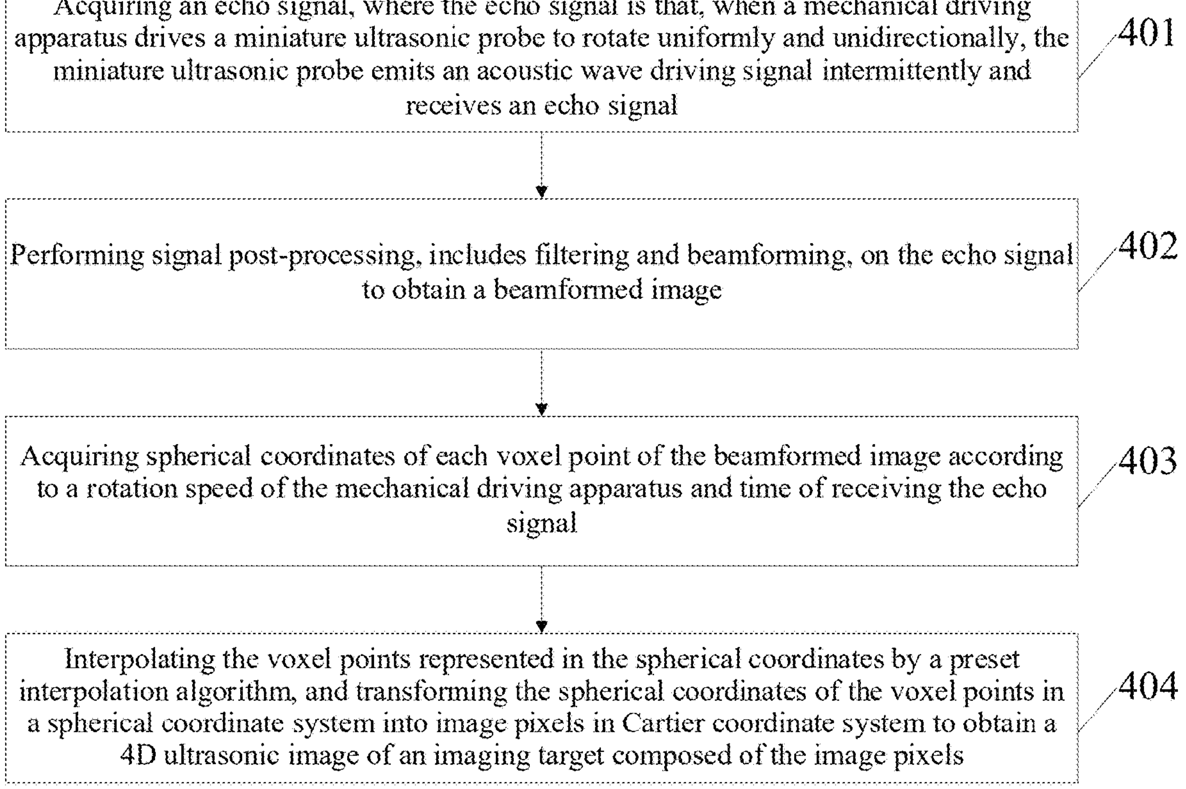
FIG. 4 is a flow chart of an ultrasonic imaging method according to an embodiment of the present disclosure.

Please referring to FIG. 4, FIG. 4 is a flow chart of an ultrasonic imaging method according to an embodiment of the present disclosure. The ultrasonic imaging method shown in FIG. 4 is applied to the 4D ICE imaging system, and includes the following steps:

401. An echo signal is acquired, where the echo signal is that, when a mechanical driving apparatus drives a miniature ultrasonic probe to rotate uniformly and unidirectionally, the miniature ultrasonic probe emits an acoustic wave driving signal intermittently and receives an echo signal.

It should be noted that an execution body of the ultrasonic imaging method may be an ultrasonic host or a workstation, which is not limited here. The ICE imaging system provided by the present disclosure is in multifunctional imaging, and can be compatible with two imaging modes: 2D ICE and 4D ICE. The 2D imaging mode can be directly completed on the portable ultrasonic host due to small amount of data and computation, and no mechanical rotation of motor, slip ring and probe is required. In the 4D imaging mode, mechanical rotation is needed, and the algorithm and post-processing are complex. The following mainly describes the 4D imaging mode. This embodiment is the 4D ultrasonic imaging, therefore, it is necessary to obtain the echoes of the emitted and received acoustic driving signals for imaging, and for ultrasonic imaging, the echo signal is the echo signal received by the miniature ultrasonic probe intermittently emitting the acoustic wave driving signal while the mechanical driving apparatus drives the miniature ultrasonic probe to rotate uniformly and unidirectionally.

Exemplary, the ultrasonic probe in this embodiment is a linear-phase array ultrasonic probe, the probe is as shown in FIG. 3 (*b*). As the probe can achieve deflection and focusing only in the two-dimensional imaging plane, an acoustic lens is used on the ultrasonic probe and rotates in the catheter. To prevent a gap between the probe and the catheter from being filled with air to affect sound permeability, normal saline is injected into the catheter. Acoustic waves are refracted in the acoustic lens to achieve geometric focusing in a direction perpendicular to the plane direction, thus improving the imaging signal-to-noise ratio and contrast at the focusing position.

The closed-loop control motor located at the proximal end of the catheter can achieve high-accuracy unidirectional rotation to drive the multichannel slip ring, the torque coil and the probe to rotate unidirectionally and uniformly in the catheter. The ultrasonic probe can perform rapid imaging while rotating unidirectionally. In order to adjust an angle of imaging field of view, a tip end of the catheter can be pulled to deflect through a bending handle and the drawing wire in the catheter.

Exemplary, the ultrasonic probe converts a received pressure signal into an analog electrical signal. The analog electrical signal is transmitted to the portable ultrasonic host through a lead wire and a slip ring, thus obtaining an acoustic wave signal. The beamforming is performed on the ultrasonic host, in general, the ultrasonic host is a field programmable gate array (FPGA for short), ultrasonic host for partial soft beamforming is on a central processing unit (CPU) or a graphics processing unit (GPU), and the data after beamforming (i.e., the image of voxel points on the beam), a deflection angle of the beam and a deflection angle of the probe are transmitted to the workstation through a high-speed data interface. The high-speed data interface includes, but is not limited to, a universal serial bus (USB), a network cable, a peripheral component interconnect express (PCI-E) and a thunderbolt. Assuming that the number of imaged beams per second is M and the construction of a three-dimensional image needs N beams, a volumetric Imaging frame rate of 4D ICE is M/N.

402. The echo signal is subjected to signal post-processing, including filtering and beamforming, to obtain a beamformed image.

Further, the obtained echo signal needs to be subjected to filtering and beamforming. Specifically, the received echo signal is subjected to signal post-processing, including filtering and beamforming, to obtain a beamformed image. Signal post-processing includes, but is not limited to, filtering, analog-digital conversion, gain, amplification, beamforming, and other signal processing.

Exemplary, the ultrasonic probe converts a received pressure signal into an analog electrical signal. The analog electrical signal is transmitted to the portable ultrasonic host through a lead wire and a slip ring, thus obtaining an acoustic wave signal. The beamforming is performed on the ultrasonic host (in general, the ultrasonic host is FPGA, ultrasonic host for partial soft beamforming is on CPU or GPU), and the data after beamforming (i.e., the image of voxel points on the beam), a deflection angle of the beam and a deflection angle of the probe are transmitted to the workstation through a high-speed data interface (e.g., USB, a network cable, PCI-E, and a thunderbolt). Assuming that the number of imaged beams per second is M and the construction of a three-dimensional image needs N beams, a volumetric Imaging frame rate of 4D ICE is M/N.

Cardiac imaging generally adopts focused ultrasound imaging, that is, each excitation and reception are in the form of linear acoustic waves, and multiple linear beams are emitted and received at different emission angles in turn to scan the whole imaging area, thus scanning and imaging the tissue. During 4D imaging, image data of multiple beams needs to be combined in the post processing to form a two-dimensional image, or a three-dimensional image (image reconstruction) which needs to be presented to doctors in real time for intraoperative guidance. Therefore, powerful computing power is required for post-processing three-dimensional reconstruction. The computing power of the traditional portable ultrasonic host is limited, while an expensive trolley ultrasonic host is usually used for the area array 4D ICE. In order to reduce the cost of the host, the portable ultrasonic host can be used in the present disclosure, and the parallel computing-based image reconstruction algorithm can be performed on the workstation, thus improving the post-processing speed.

403. Spherical coordinates of each voxel point of the beamformed image are acquired according to a rotation speed of the mechanical driving apparatus and time of receiving the echo signal.

It should be noted that a voxel point P in the beamformed image is expressed as $(\rho, \theta, \varphi)$ in a spherical coordinate system, where $\rho$ is a distance from the voxel to the center of the probe, $\theta$ is a deflection angle of scanning in an imaging plane, and $\varphi$ is a deflection angle of mechanical rotation of the probe. Therefore, the spherical coordinates of each voxel point of the beamformed image can be determined according to the rotation speed of the mechanical driving apparatus and time of receiving the echo signal.

The voxel points expressed in the spherical coordinates are interpolated by a preset interpolation algorithm, and the spherical coordinates of the voxel points in a spherical coordinate system are transformed into image pixels in Cartesian coordinate system to obtain a 4D ultrasonic image of an imaging target composed of image pixels.

Further, the image pixels can be obtained by converting the spherical coordinates into Cartesian coordinate system, thus achieving the reconstruction of the 4D ultrasonic imaging. Specifically, the voxel points expressed in the spherical coordinates are interpolated by a preset interpolation algorithm to determine the image pixels of the voxel points in the Cartesian coordinate system, thus obtaining a 4D ultrasonic image of an imaging target composed of the image pixels.

It may be understood that the 4D ultrasonic images of the imaging target may also be displayed on the ultrasonic host or other display modules with display capability, thus providing surgical guidance for medical staff during interventional procedure and better navigate during surgery.

Figure 5:
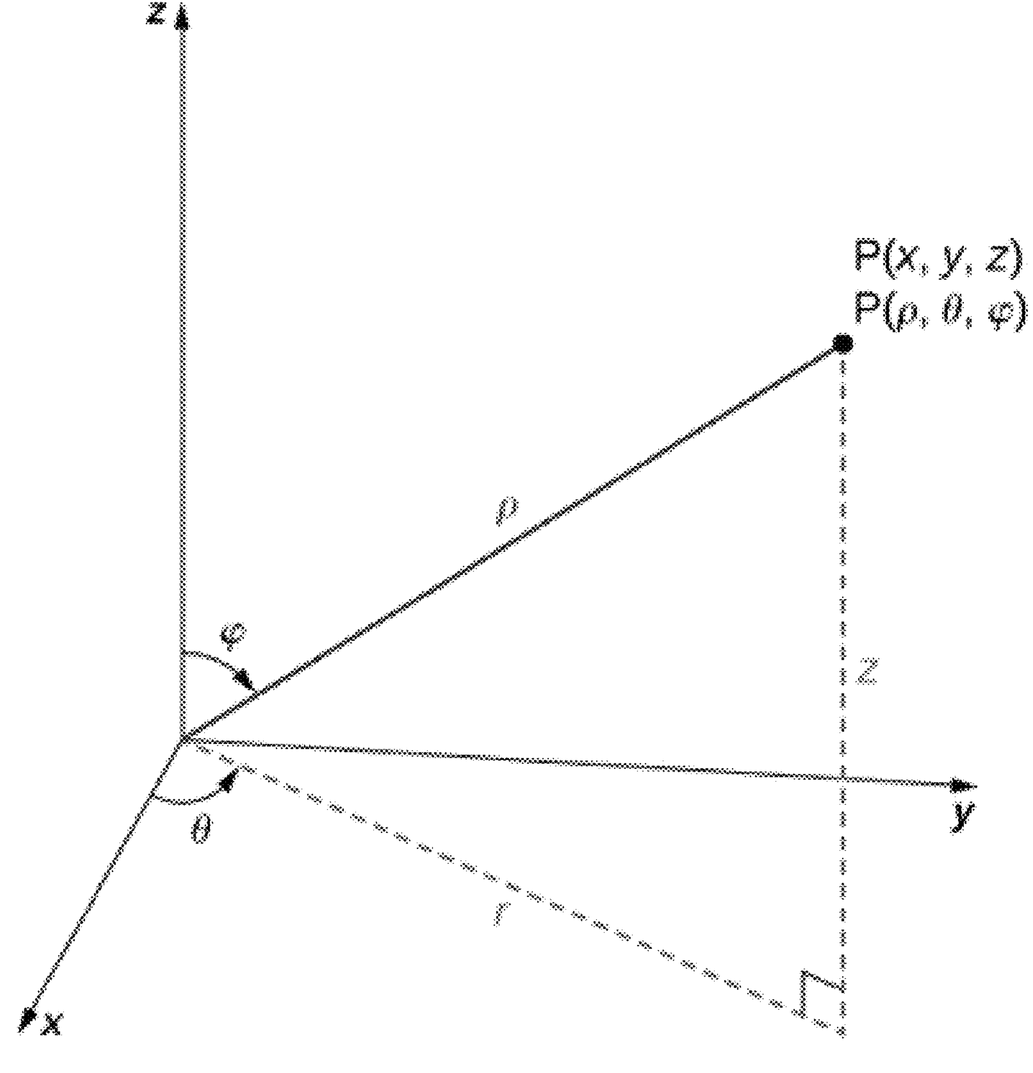
FIG. 5 is a schematic diagram of spherical coordinates and Cartesian coordinate system according to an embodiment of the present disclosure.

Exemplary, FIG. 5 is a schematic diagram of spherical coordinates and Cartesian coordinate system according to an embodiment of the present disclosure. The voxel point P is expressed as (ρ, θ, φ) in the spherical coordinate system: ρ is a distance from the voxel to the center of the probe, θ is a deflection angle of scanning in the imaging plane, and φ is a deflection angle of mechanical rotation of the probe. Point P is expressed as (x, y, z) in the Cartesian coordinate system.

It should be noted that under the 4D imaging mode of this embodiment, spherical coordinate data collected by multiple ultrasonic beam imaging needs to be transmitted to an internal memory of the workstation by the portable ultrasonic host, and the data is reconstructed as an image in the Cartesian coordinate system through three-dimensional interpolation. According to the convention, the array elements of the probe are arranged along the x axis and the probe rotates around the x axis. As shown in FIG. 4, the algorithm has the characteristics of large amount of data and simple operation of a single thread, and is suitable for parallel computing. The following is an interpolation 3D reconstruction algorithm based on high-performance parallel computing.

Assuming that the number of focused beams imaged per second is M, an electronic deflection angle of adjacent beams in the imaging plane is d_θ, and a mechanical deflection angle in the rotation direction is d_φ. Any position on any beam is expressed as $(\rho_1, \theta_1, \varphi_1), \ldots, (\rho_M, \theta_M, \varphi_M)$ by the spherical coordinates, where ρ cannot exceed the maximum imaging depth.

Under a parallel computing framework, each thread is used to compute each voxel in the Cartesian coordinate system. That is, each voxel on the three-dimensional image, which is expressed as a grid in the Cartesian coordinate system with coordinates as (x,y,z), is transformed to be expressed by a spherical coordinate system according to the following formula:

$$\rho = \sqrt{x^2 + y^2 + z^2}$$

$$\theta = a\tan\left(\frac{y}{x}\right)$$

$$\varphi = a\sin\left(\frac{\sqrt{x^2 + y^2}}{\rho}\right)$$

Interpolation calculation is performed on each thread. For simplification, trilinear interpolation calculation is used in the present disclosure, that is, assuming $\rho_i < \rho \leq \rho_{i+1}$, $\theta_j < \theta \leq \theta_{j+1}$, $\varphi_k < \varphi \leq \varphi_{k+1}$, the interpolation algorithm includes the following mathematical expressions:

$$C = V(\rho_i, \theta_j, \varphi_k)(1-\rho_d)(1-\theta_d)(1-\varphi_d) + V(\rho_{i+1}, \theta_j, \varphi_k)\rho_d(1-\theta_d)(1-\varphi_d) + V(\rho_i, \theta_j, \varphi_{k+1})(1-\rho_d)(1-\theta_d)\varphi_d + V(\rho_{i+1}, \theta_j, \varphi_{k+1})\rho_d(1-\theta_d)\varphi_d + V(\rho_i, \theta_{j+1}, \varphi_k)(1-\rho_d)\theta_d(1-\varphi_d) + V(\rho_{i+1}, \theta_j + 1, \varphi_k)\rho_d\theta_d(1-\varphi_d) + V(\rho_i, \theta_{j+1}, \varphi_{k+1})(1-\rho_d)\theta_d\varphi_d + V(\rho_{i+1}, \theta_j + 1, \varphi_k)\rho_d\theta_d\varphi_d:$$

where $\rho_d = (\rho - \rho_i)/(\rho_{i+1} - \rho_i)$, $\theta_d = (\theta - \theta_j)/(\theta_{j+1} - \theta_j)$, $\rho_d = (\varphi - \varphi_k)/(\varphi_{k+1} - \varphi_k)$, $(\rho_i, \Lambda_j, \varphi_k)$ is the spherical coordinates, C are image pixels on the Cartesian coordinate system (x, y, z).

The above i+1, j+1 and k+1 are all coordinate points near i, j, k, which are used to determine the image pixels in Cartesian coordinate system (x, y, z) by interpolation calculation.

Other interpolation algorithms, such as Kriging interpolation, polynomial interpolation, and spline function interpolation, can also be used for the above trilinear interpolation. The above ultrasonic imaging method can be achieved on GPU workstation, or multi-core CPU or FPGA, which can greatly improve the post-processing efficiency of 3D interpolation reconstruction and achieve 4D cardiac imaging, thus navigating during operation better.

An ultrasonic imaging method is provided, which is applied to the 4D ICE imaging system in the first aspect or according to any feasible implementation mode. The ultrasonic imaging method includes the following steps: acquiring an echo signal, where the echo signal is that, when a mechanical driving apparatus drives a miniature ultrasonic probe to rotate uniformly and unidirectionally, the miniature ultrasonic probe emits an acoustic wave driving signal intermittently and receives an echo signal; performing signal post-processing which includes filtering and beamforming on the echo signal to obtain a beamformed image; acquiring spherical coordinates of each voxel point of the beamformed image according to a rotation speed of the mechanical driving apparatus and time of receiving the echo signal; and interpolating the voxel points expressed in the spherical coordinates by a preset interpolation algorithm, and transforming the spherical coordinates of the voxel points in a spherical coordinate system into image pixels in Cartesian coordinate system to obtain a 4D ultrasonic image of an imaging target composed of the image pixels. Through above method, the ultrasonic imaging of an imaging target can be achieved, and through a three-dimensional reconstruction algorithm based on high-performance parallel computing, the three-dimensional reconstruction, rendering and other algorithms requiring high computing power can be completed on a back-end parallel computing workstation (such as GPU), so the portable ultrasonic host with low cost can be used and the device cost of the hospital can be reduced.

In conclusion, a mechanical 4D ICE scheme provided by the present disclosure, compared with the area array 4D ICE scheme, has the following advantages: 1. The cost of mechanical 4D ICE is about 10% of that of the area array 4D ICE scheme, and but the mechanical 4D ICE scheme has the same image quality as the area array 4D ICE scheme. 2. The mechanical 4D ICE scheme can achieve the maximum 360° imaging field of view in the rotation direction, and the imaging field of view is larger than that of the area array 4D ICE. 3. The mechanical 4D ICE scheme can use a portable ultrasonic host with low cost, and thus the admission cost is reduced. 4. The mechanical 4D ICE scheme, compared with an electronic 4D probe, has less probe heating, and is safer to a patient.

Figure 6:
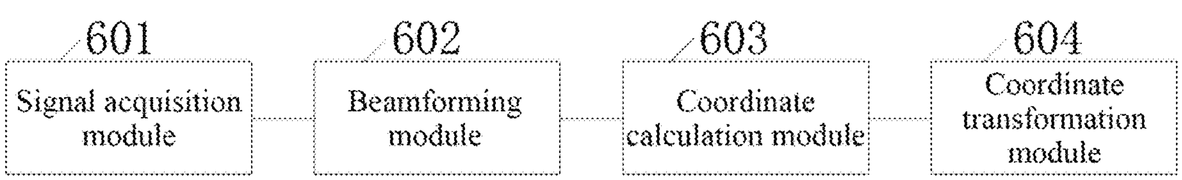
FIG. 6 is a structural block diagram of an ultrasonic imaging apparatus according to an embodiment of the present disclosure.

Please referring to FIG. 6, FIG. 6 is a structural block diagram of an ultrasonic imaging apparatus according to an embodiment of the present disclosure. The ultrasonic imaging apparatus shown in FIG. 6 includes:

a signal acquisition signal 601, used to acquire an echo signal, where the echo signal is that, when a mechanical driving apparatus drives a miniature ultrasonic probe to rotate uniformly and unidirectionally, the miniature ultrasonic probe emits an acoustic wave driving signal intermittently and receives an echo signal;

a beamforming module 602, used to perform signal post-processing which includes filtering and beamforming on the echo signal to obtain a beamformed image;

a coordinate calculation module 603, used to acquire spherical coordinates of each voxel point of the beamformed image according to a rotation speed of the mechanical driving apparatus and time of receiving the echo signal; and a coordinate transformation module 604, used to interpolate the voxel points represented in the spherical coordinates by a preset interpolation algorithm, and transform the spherical coordinates of the voxel points in a spherical coordinate system into image pixels in Cartesian coordinate system to obtain a 4D ultrasonic image of an imaging target composed of the image pixels.

It should be noted that the apparatus shown in FIG. 6 has the similar content to the method shown in FIG. 4, and thus will not be described in detail here for avoiding repetition, specifically referring to the content of the method shown in FIG. 4.

Further, in order to ensure the image display effect, the apparatus may also include a rendering and display module, used to display the obtained 4D ultrasonic image on a display in real time and to perform 3D rendering.

The ultrasonic imaging apparatus provided by the present disclosure includes a signal acquisition signal, used to acquire an echo signal, where the echo signal is that, when a mechanical driving apparatus drives a miniature ultrasonic probe to rotate uniformly and unidirectionally, the miniature ultrasonic probe emits an acoustic wave driving signal intermittently and receives an echo signal; a beamforming module, used to perform signal post-processing which includes filtering and beamforming on the echo signal to obtain a beamformed image; a coordinate calculation module, used to acquire spherical coordinates of each voxel point of the beamformed image according to a rotation speed of the mechanical driving apparatus and time of receiving the echo signal; and a coordinate transformation module, used to interpolate the voxel points represented in the spherical coordinates by a preset interpolation algorithm, and transform the spherical coordinates of the voxel points in a spherical coordinate system into image pixels in Cartesian coordinate system to obtain a 4D ultrasonic image of an imaging target composed of the image pixels. Through above apparatus, the ultrasonic imaging of an imaging target can be achieved, and through a three-dimensional reconstruction algorithm based on high-performance parallel computing, the three-dimensional reconstruction, rendering and other algorithms requiring high computing power can be completed on a back-end parallel computing workstation (such as GPU or CPU), so the portable ultrasonic host with low cost can be used and the device cost of the hospital can be reduced.

Figure 7:
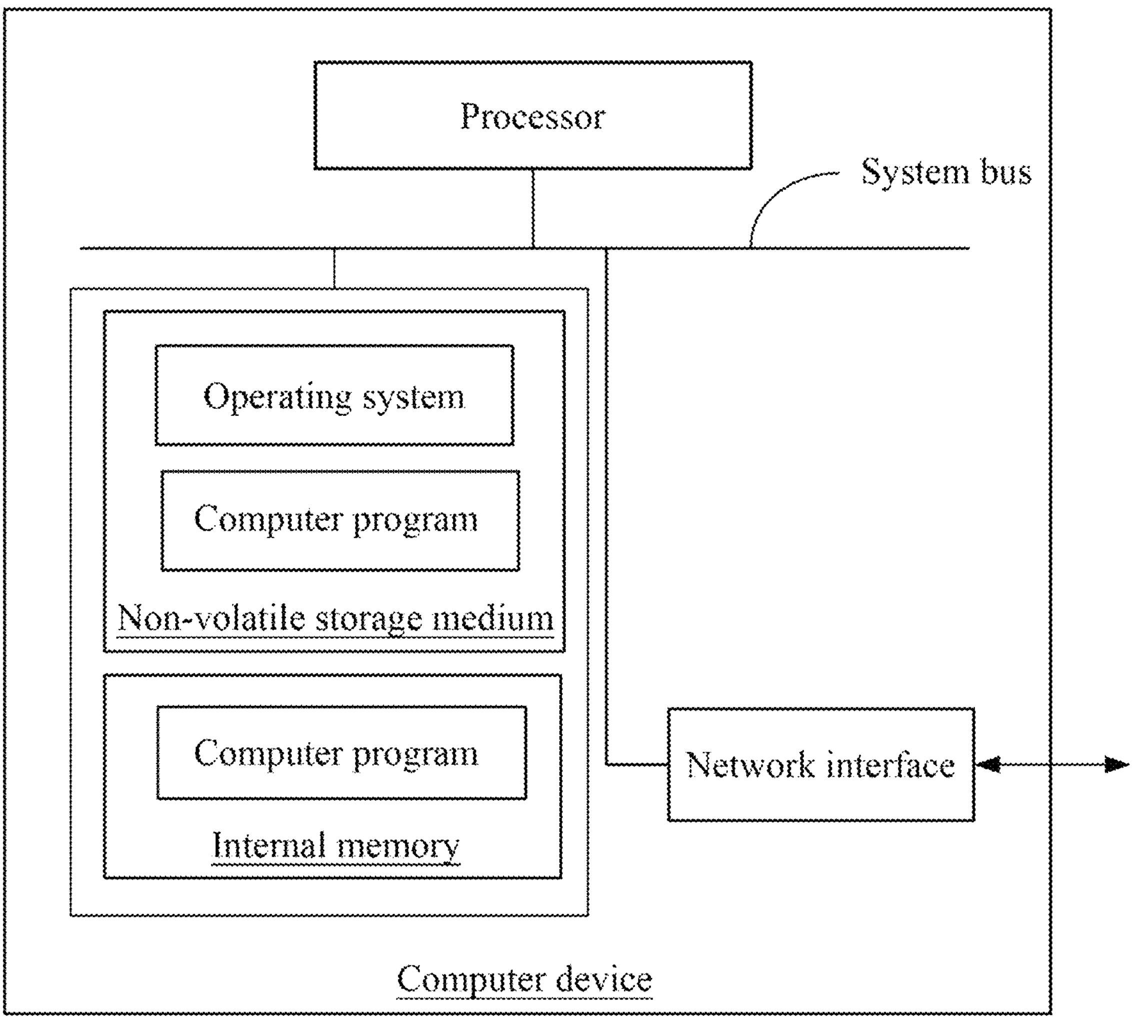
FIG. 7 is a structural block diagram of a computer device according to an embodiment of the present disclosure.

FIG. 7 is a diagram of an internal structure of a computer device according to an embodiment. The computer device may specifically be a terminal, or a server. As shown in FIG. 7, the computer device includes a processor, a memory and a network interface which are connected by a system bus. The memory includes a non-volatile storage medium, and an internal memory. The non-volatile storage medium of the computer device stores an operating system, and can also store a computer program. The computer program, when executed by the processor, can make the processor implement the above method. The computer program may also be stored in the internal memory. The computer program, when executed by a processor, enables the processor to execute the above method. Those skilled in the part may understand that the structure shown in FIG. 7 is only a block diagram of a part of the structure related to the scheme of the present disclosure, and does not constitute a limitation on the computer device to which the scheme of the present disclosure is applied. The specific computer device may include more or less components than those shown in the figure, or combine some components, or have different component arrangements.

In one embodiment, a computer device is further disclosed, including a memory, and a processor. A computer program is stored in the memory, and the computer program, when executed by the processor, enables the processor to execute method shown in FIG. 4.

In one embodiment, a computer readable storage medium is further disclosed, and a computer program is stored in the computer readable storage medium. The computer program, when executed by a processor, enables the processor to execute the method shown in FIG. 4.

Those skilled in the art can understand that all or part of the processes in the method for implementing the above embodiments can be completed by instructing related hardware through the computer program, which can be stored in a nonvolatile computer-readable storage medium, and the program, when executed, may include the processes of the above embodiments. Any reference to memory, storage, database or other media used in the embodiments provided in the present disclosure may include non-volatile and/or volatile memory. The non-volatile memory may include a read-only memory (ROM), a programmable ROM (PROM), an electrically programmable ROM (EPROM), an electrically erasable programmable ROM (EEPROM), or a flash memory. The volatile memory may include a random access memory (RAM), or an external cache memory. By way of illustration than limitation, RAM is available in various forms, such as static RAM (SRAM), dynamic RAM (DRAM), synchronous DRAM (SDRAM), double data rate SDRAM (DDRSDRAM), enhanced SDRAM (ESDRAM), synchlink DRAM (SLDRAM), memory bus (Rambus) direct RAM (RDRAM), and direct rambus dynamic RAM (DRDRAM), and rambus dynamic RAM (RDRAM).

The technical features of the above embodiments can be combined at will. In order to make the description concise, not all possible combinations of the technical features in the above embodiments are described. However, it should be considered that these combinations of technical features fall within the scope recorded in this specification provided that these combinations of technical features do not have any conflict.

The foregoing embodiments only describe several implementation modes of the present disclosure, and their description is specific and detailed, but cannot therefore be understood as a limitation to the patent scope of the present disclosure. It should be noted that for those of ordinary skill in the art, several deformations and improvements can be made without departing from the concept of the present disclosure, all of which fall within the scope of protection of the present disclosure. Therefore, the scope of protection of the patent of the present disclosure shall be subject to the appended claims.

What is claimed is:

1. A 4D (four-dimensional) intracardiac echocardiography (ICE) imaging system, at least comprising an interventional catheter, mechanical driving apparatus and an ultrasonic host, wherein the interventional catheter comprises a cavity located at a distal end, and a miniature ultrasonic probe located in the cavity, and the mechanical driving apparatus is arranged at a proximal end of the interventional catheter; the mechanical driving apparatus and the ultrasonic host are connected to the miniature ultrasonic probe, respectively;

- the ultrasonic host is used to output an acoustic wave driving signal;
- the miniature ultrasonic probe is used to intermittently emit the acoustic wave driving signal output by the ultrasonic host;
- the mechanical driving apparatus is used to drive the miniature ultrasonic probe to rotate unidirectionally and uniformly inside the interventional catheter when the miniature ultrasonic probe emits the acoustic wave driving signal output by the ultrasonic host, thus performing mechanical 4D scanning imaging on different positions of an imaging target;
- the miniature ultrasonic probe is also used to receive an echo signal of the acoustic wave driving signal, and to transmit the received echo signal to the ultrasonic host; and the ultrasonic host is also used to perform signal post-processing on the received echo signal to determine 4D ultrasonic imaging of the imaging target;
- further comprising a torque coil and a catheter-side connector; the torque coil is arranged in the cavity of the interventional catheter and fixedly connected to the miniature ultrasonic probe, and the torque coil is fixedly connected to the catheter-side connector, and the catheter-side connector rotates to drive the torque coil and the probe to rotate; and the miniature ultrasonic probe, the torque coil and the catheter-side connector are all disposable; and
- wherein the mechanical driving apparatus comprises a motor, a multichannel slip ring, and a host-side connector; the motor is fixedly connected to a stator of the multichannel slip ring, the host-side connector is fixedly connected to a rotor of the multichannel slip ring, the host-side connector is connected to the catheter-side connector, the motor drives the rotor of the multichannel slip ring to rotate through mechanical transmission, and the motor, the multichannel slip ring and the host-side connector are all reusable.

2. The 4D ICE imaging system according to claim 1, wherein an inner wall of the interventional catheter comprises at least four drawing wires with an interval of 90°, the proximal end of the interventional catheter is also provided with a handle, and the handle is used to pull at least one of the drawing wires to adjust tightness of the drawing wire, thus achieving the bending of the miniature ultrasonic probe in four directions.

3. The 4D ICE imaging system according to claim 1, wherein the miniature ultrasonic probe is a two-dimensional imaging phased array probe, or a plurality of two-dimensional imaging phased array probes combined at a preset spatial angle.

4. The 4D ICE imaging system according to claim 3, wherein the miniature ultrasonic probe comprises a transducer, and an acoustic lens; and the acoustic lens is used to focus an ultrasonic wave emitted by the transducer to enhance a signal-to-noise ratio of the ultrasonic wave at a focusing position.

5. The 4D ICE imaging system according to claim 4, wherein the cavity of the interventional catheter is filled with normal saline in a manner of filling the normal saline into the cavity at the distal end of the interventional catheter through a syringe at the proximal end of the interventional catheter, thus achieving acoustic coupling between the transducer and an outer sheath of the interventional catheter.

6. An ultrasonic imaging method, wherein the ultrasonic imaging method is applied to the 4D ICE imaging system according to claim 1, and comprises the following steps:

- acquiring the echo signal, wherein the echo signal is that, when the mechanical driving apparatus drives a miniature ultrasonic probe to rotate uniformly and unidirectionally, the miniature ultrasonic probe emits an acoustic wave driving signal intermittently and receives an echo signal;
- performing signal post-processing which comprises filtering and beamforming on the echo signal to obtain a beamformed image;
- acquiring spherical coordinates of each voxel point of the beamformed image according to a rotation speed of the mechanical driving apparatus and time of receiving the echo signal; and
- interpolating the voxel points expressed in the spherical coordinates by a preset interpolation algorithm, and transforming the spherical coordinates of the voxel points in a spherical coordinate system into image pixels in Cartesian coordinate system to obtain a 4D ultrasonic image of an imaging target composed of the image pixels;
- the interpolation algorithm comprises the following mathematic expressions:

$$C = V(\rho_i, \theta_j, \varphi_k)(1-\rho_d)(1-\theta_d)(1-\varphi_d) + V(\rho_{i+1}, \theta_j, \varphi_k)\rho_d(1-\theta_d)(1-\varphi_d) + V(\rho_i, \theta_j, \varphi_{i+1})(1-\rho_d)(1-\theta_d)\varphi_d + V(\rho_{i+1}, \theta_j, \varphi_{k+1})\rho_d(1-\theta_d)\varphi_d + V(\rho_i, \theta_{j+1}, \varphi_k)(1-\rho_d)\theta_d(1-\varphi_d) + V(\rho_{i+1}, \theta_j+1, \varphi_k)\rho_d\theta_d(1-\varphi_d) + V(\rho_i, \theta_{j+1}, \varphi_{k+1})(1-\rho_d)\theta_d\varphi_d + V(\rho_{i+1}, \theta_j+1, \varphi_k)\rho_d\theta_d\varphi_d:$$

wherein $\rho_d=(\rho-\rho_j)/(\rho_{i+1}-\rho_j)$, $\theta_d=(\theta-\theta_j)/(\theta_{j+1}-\theta_j)$, $\varphi_d=(\varphi-\varphi_k)/(\varphi_{k+1}-\varphi_k)$, $(\rho_i, \theta_j, \varphi_k)$ is the spherical coordinates, C are image pixels on the Cartesian coordinate system (x, y, z); $V(\rho_j, \theta_j, \varphi_k)$ is the value of the voxel point in the spherical coordinate system.

7. An ultrasonic imaging apparatus, comprising:

- a signal acquisition module, used to acquire an echo signal, wherein the echo signal is that, when a mechanical driving apparatus drives a miniature ultrasonic probe to rotate uniformly and unidirectionally, the miniature ultrasonic probe emits an acoustic wave driving signal intermittently and receives an echo signal;
- a beamforming module, used to perform signal post-processing which comprises filtering and beamforming on the echo signal to obtain a beamformed image;
- a coordinate calculation module, used to acquire spherical coordinates of each voxel point of the beamformed image according to a rotation speed of the mechanical driving apparatus and time of receiving the echo signal; and a coordinate transformation module, used to interpolate the voxel points represented in the spherical coordinates by the preset interpolation algorithm, and transform the spherical coordinates of the voxel points in a spherical coordinate system into image pixels in Cartier coordinate system to obtain a 4D ultrasonic image of an imaging target composed of image pixels.

* * * * *